United States Patent [19]

Itaya et al.

[11] Patent Number: 5,770,178
[45] Date of Patent: Jun. 23, 1998

[54] METAL CHELATE FORMING PEPTIDES AND USE THEREOF

[75] Inventors: Yoshitoshi Itaya, Sodegaura; Ikuya Seki, Ichihara; Koichi Hanaoka, Sodeqaura; Yoshifumi Shirakami, Ichihara, all of Japan

[73] Assignee: Nihon Medi-Physics Co., Ltd., Hyogo-Ken, Japan

[21] Appl. No.: 575,863

[22] Filed: Dec. 20, 1995

[30] Foreign Application Priority Data

Dec. 27, 1994 [JP] Japan .................................... 6-338024

[51] Int. Cl.$^6$ .......................... A61K 51/00; A61M 36/14
[52] U.S. Cl. ...................... 424/1.69; 424/1.11; 424/1.65; 534/14; 530/300; 530/331
[58] Field of Search ................................ 424/1.11, 1.65, 424/1.69, 9.1, 9.3, 9.32, 9.4, 9.42, 9.5; 530/300, 324–330, 331; 534/10–16

[56] References Cited

U.S. PATENT DOCUMENTS

| | | | |
|---|---|---|---|
| 5,277,892 | 1/1994 | Rhodes | 424/1.69 |
| 5,443,816 | 8/1995 | Zamora et al. | 424/1.69 |
| 5,464,934 | 11/1995 | Dunn et al. | 530/326 |
| 5,508,020 | 4/1996 | Dean et al. | 424/1.69 |
| 5,552,525 | 9/1996 | Dean . | |
| 5,556,609 | 9/1996 | Zamora | 424/1.69 |
| 5,561,220 | 10/1996 | Dean et al. . | |
| 5,591,593 | 1/1997 | Courtenay-Luck . | |

FOREIGN PATENT DOCUMENTS

| | | |
|---|---|---|
| 0649857 | 10/1994 | European Pat. Off. . |
| 0700930 | 3/1996 | European Pat. Off. . |
| 0719790 | 3/1996 | European Pat. Off. . |
| 4-346998 | 12/1992 | Japan ................................ C07K 5/10 |
| 4-346999 | 12/1992 | Japan ................................ C07K 7/06 |
| WO 92/13572 | 8/1992 | WIPO ............................ A61K 49/02 |
| 9218534 | 10/1992 | WIPO . |
| WO 94/19024 | 9/1994 | WIPO ............................ A61K 49/00 |
| WO 94/26295 | 11/1994 | WIPO ............................ A61K 37/02 |
| 9501188 | 1/1995 | WIPO . |

OTHER PUBLICATIONS

Pearson et al, *J. Med. Chem.* 39(7):1361–1371 (1996).
6th World Congress of Nuclear Medicine and Biology, Oct. 23–28, 1994, S46.
Knight et al. Thrombus Imaging with Technetium–99m Syntheic Peptides Based upon the Binding–Domain of a Monoclonal Antibody to Activated Platelets, Feb. 1994, vol. 35 No. 2.

*Primary Examiner*—John Kight
*Assistant Examiner*—Dameron Jones
*Attorney, Agent, or Firm*—Sughrue, Mion, Zinn, Macpeak & Seas, PLLC

[57] ABSTRACT

The invention provides a metal chelate forming peptide having an amino acid sequence of three amino acid residues represented by: X1-X2-Cys, wherein X1 represents an amino acid residue other than Cys residue; X2 represents an amino acid residue other than Cys residue and Pro residue; functional groups at the N-terminus, C-terminus and side chain may be substituted with protecting groups; and each of the amino acid residues may be any of D-form and L-form. Further, the invention provides a complex of the peptide with a physiologically active peptide, protein or other substance; a labeled reagent obtained by labeling the peptide or the complex with a metal radionuclide; and a radiodiagnostic and radiotherapeutic composition comprising the metal radionuclide-labeled reagent.

14 Claims, 5 Drawing Sheets

Tumor

FIG. 5

Tumor

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 1:

Lys  Cys  Thr  Cys  Cys  Ala
                         5

( 2 ) INFORMATION FOR SEQ ID NO: 2:

( i ) SEQUENCE CHARACTERISTICS:
        ( A ) LENGTH: 18 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 2:

```
Lys Tyr Cys Ala Arg Glu Pro Pro Thr Arg
                  5                   10
Thr Phe Ala Tyr Trp Gly Gln Gly
                 15
```

( 2 ) INFORMATION FOR SEQ ID NO: 3:

( i ) SEQUENCE CHARACTERISTICS:
        ( A ) LENGTH: 18 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 3:

```
Lys Tyr Cys Ala Arg Glu Pro Pro Thr Arg
                  5                   10
Thr Asn Ala Tyr Trp Gly Gln Gly
                 15
```

( 2 ) INFORMATION FOR SEQ ID NO: 4:

( i ) SEQUENCE CHARACTERISTICS:
        ( A ) LENGTH: 21 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 4:

```
Lys Tyr Cys Gly Gly Lys Thr Lys Pro Arg Glu Gln
                  5                   10
Gln Tyr Asn Ser Thr Tyr Arg Val Val
                 15              20
```

( 2 ) INFORMATION FOR SEQ ID NO: 5:

( i ) SEQUENCE CHARACTERISTICS:
        ( A ) LENGTH: 15 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 5:

```
Ala Arg Glu Pro Pro Thr Arg Thr Phe Ala
                  5                   10
Tyr Trp Gly Gln Gly
                 15
```

( 2 ) INFORMATION FOR SEQ ID NO: 6:

( i ) SEQUENCE CHARACTERISTICS:
        ( A ) LENGTH: 16 amino acids
        ( B ) TYPE: amino acid
        ( D ) TOPOLOGY: linear (ii) MOLECULE TYPE: protein (xi) SEQUENCE DESCRIPTION: SEQ ID NO: 6:

```
Lys  Thr  Lys  Pro  Arg  Glu  Gln  Gln  Tyr  Asn  Ser  Thr
                         5                        10
Tyr  Arg  Val  Val
              15
```

(2) INFORMATION FOR SEQ ID NO: 7:

(i) SEQUENCE CHARACTERISTICS:
        (A) LENGTH: 18 amino acids
        (B) TYPE: amino acid
        (D) TOPOLOGY: linear     (ii) MOLECULE TYPE: protein     (xi) SEQUENCE DESCRIPTION: SEQ ID NO: 7:

```
Asp  Tyr  Cys  Ala  Arg  Glu  Pro  Pro  Thr  Arg
                         5                        10
Thr  Phe  Ala  Tyr  Trp  Gly  Gln  Gly
                    15
```

(2) INFORMATION FOR SEQ ID NO: 8:

(i) SEQUENCE CHARACTERISTICS:
        (A) LENGTH: 18 amino acids
        (B) TYPE: amino acid
        (D) TOPOLOGY: linear     (ii) MOLECULE TYPE: protein     (xi) SEQUENCE DESCRIPTION: SEQ ID NO: 8:

```
Tyr  Tyr  Cys  Ala  Arg  Glu  Pro  Pro  Thr  Arg
                         5                        10
Thr  Phe  Ala  Tyr  Trp  Gly  Gln  Gly
                    15
```

(2) INFORMATION FOR SEQ ID NO: 9:

(i) SEQUENCE CHARACTERISTICS:
        (A) LENGTH: 18 amino acids
        (B) TYPE: amino acid
        (D) TOPOLOGY: linear     (ii) MOLECULE TYPE: protein     (xi) SEQUENCE DESCRIPTION: SEQ ID NO: 9:

```
Lys  Gly  Cys  Ala  Arg  Glu  Pro  Pro  Thr  Arg
                         5                        10
Thr  Phe  Ala  Tyr  Trp  Gly  Gln  Gly
                    15
```

(2) INFORMATION FOR SEQ ID NO: 10:

(i) SEQUENCE CHARACTERISTICS:
        (A) LENGTH: 18 amino acids
        (B) TYPE: amino acid
        (D) TOPOLOGY: linear     (ii) MOLECULE TYPE: protein     (xi) SEQUENCE DESCRIPTION: SEQ ID NO: 10:

```
Lys  Pro  Cys  Ala  Arg  Glu  Pro  Pro  Thr  Arg
                         5                        10
```

```
            Thr  Phe  Ala  Tyr  Trp  Gly  Gln  Gly
                                1 5
```

( 2 ) INFORMATION FOR SEQ ID NO: 11:

( i ) SEQUENCE CHARACTERISTICS:
         ( A ) LENGTH: 18 amino acids
         ( B ) TYPE: amino acid
         ( D ) TOPOLOGY: linear ( i i ) MOLECULE TYPE: protein ( x i ) SEQUENCE DESCRIPTION: SEQ ID NO: 11:

```
            Tyr  Lys  Cys  Ala  Arg  Glu  Pro  Pro  Thr  Arg
                                 5                          1 0

Thr  Phe  Ala  Tyr  Trp  Gly  Gln  Gly
                                1 5
```

( 2 ) INFORMATION FOR SEQ ID NO: 12:

( i ) SEQUENCE CHARACTERISTICS:
         ( A ) LENGTH: 18 amino acids
         ( B ) TYPE: amino acid
         ( D ) TOPOLOGY: linear ( i i ) MOLECULE TYPE: protein ( x i ) SEQUENCE DESCRIPTION: SEQ ID NO: 12:

```
            Gly  Gly  Lys  Thr  Lys  Pro  Arg  Glu  Gln  Gln  Tyr
                                 5                               1 0

Asn  Ser  Thr  Tyr  Arg  Val  Val
                                1 5
```

METAL CHELATE FORMING PEPTIDES AND USE THEREOF

BACKGROUND OF THE INVENTION

1. Field of the Invention

The present invention relates to a metal chelate forming peptide and use thereof. More particularly, the present invention relates to a stable metal chelate forming peptide which can provide a metal radionuclide-labeled physiologically active peptide, protein or other substance useful for radiodiagnostic and/or radiotherapeutic agents. The metal chelate forming peptide is bound to a physiologically active peptide, protein or other substance such as a peptide having affinity for a focus site in a mammalian body, to form a complex which is used as radiodiagnostic and/or radiotherapeutic agents.

2. Description of the Related Art

As amino acid sequences capable of forming chelates with metal radionuclides, there are known Lys-Cys-Thr-Cys-Cys-Ala (SEQ ID NO:1) (Linda C. Knight, J. Nucl. Med., 35 (2), 282–288, Feb. 1994) and Cys(Acm)-Gly-Cys (Acm) (DEAN, Richard, T., WO 92/13572) and the like.

Lys-Cys-Thr-Cys-Cys-Ala (SEQ ID NO:1) contains many Cys residues having a mercapto group in the molecule, and hence tends to readily form intramolecular or intermolecular disulfide bonds. Accordingly, the peptide requires a very careful handling when used for radiodiagnosis or radiotherapeutics.

Cys(Acm)-Gly-Cys(Acm) is improved to avoid the formation of intramolecular or intermolecular disulfide bonds between mercapto group-containing Cys residues, owing to protecting the mercapto group with an acetamidomethyl (Acm) group. On the other hand, the protection of such functional groups, however, invites suppressed reactivity of Cys residues, and in turn necessitates an additional heating treatment for labeling the peptide with a metal radionuclide such as Tc-99m. Furthermore, these peptides encounter the problem that metal radionuclide-labeled peptides tend to cause non-specific accumulation in the kidney within a mammalian body.

Other amino acid sequences which have been also reported as sequences capable of forming a chelate complex with a metal radionuclide are Gly-Gly-Cys (S. J. Mather et al., Eur. J. Nucl. Med. (1994) 21, Suppl. S46) and Cys-Gly-His, Asp-Gly-Cys, Glu-Gly-Cys, Gly-Asp-Cys, Gly-Glu-Cys, etc. (DUNN, T., Jeffrey, WO 94/26295). These amino acid sequences are designed to have Asp and Gly adjacent with each other, Gly and Gly adjacent with each other, or Glu and Gly adjacent with each other.

In view of the foregoing state of the art, the present invention provides a metal chelate forming peptide which is capable of readily labeling a physiologically active peptide, protein or other substance without any special treatment such as heating, to form a labeled reagent stably both in vitro and in vivo, which does not cause non-specific accumulation in the in vivo distribution, when administered to a mammal. The present invention also provides use of such a metal chelate forming peptide in radiodiagnosis and radiotherapeutics.

SUMMARY OF THE INVENTION

The present inventors have made extensive studies on the property of an amino acid sequence that is required for the metal ligand of radionuclide, and found out that a specific amino acid sequence containing Cys residue can readily bind to a metal without any particular treatment such as heating, to form a stably labeled complex.

It is therefore an object of the present invention to provide a metal chelate forming peptide having an amino acid sequence represented by:

X1-X2-Cys wherein X1 represents an amino acid residue other than Cys residue; X2 represents an amino acid residue other than Cys residue and Pro residue; functional groups at the N-terminus, C-terminus and side chain may be optionally substituted with protecting groups; and each of the amino acid residues may be either D-form or L-form.

Another object of the present invention is to provide a complex of the metal chelate forming peptide with a physiologically active peptide, protein or other substance.

A further object of the present invention is to provide a metal radionuclide-labeled reagent, wherein a metal radionuclide is coordinated to the metal chelate forming peptide or the above complex.

A still further object of the present invention is to provide a radiodiagnostic composition, which comprises as an active ingredient a metal radionuclide-labeled reagent, wherein any one of Tc-99m, In-111 and Ga-67 is coordinated to the metal chelate forming peptide or the above complex.

A still further object of the present invention is to provide a radiotherapeutic composition, which comprises as an effective ingredient a metal radionuclide-labeled reagent, wherein any one of Y-90, Re-186 and Re-188 is coordinated to the metal chelate forming peptide or the above complex.

A still further object of the present invention is to provide a method for diagnosis, which comprises the steps of:
   administering to a mammal an effective dose of the above metal radionuclide-labeled reagent wherein any one of Tc-99m, In-111 and Ga-67 is coordinated; and
   detecting the reagent localized within the mammalian body.

A still further object of the present invention is to provide use of the metal chelate forming peptide for labeling a physiologically active peptide, protein or other substance with a metal radionuclide.

A still other object of the present invention is to provide a method for preparing the metal chelate forming peptide, which comprises the steps of:
   binding cysteine or a protected derivative thereof to an amino acid X2 or a protected derivative thereof to form a dipeptide of X2-Cys; and
   binding to the thus formed dipeptide an amino acid X1 or a protected derivative thereof.

A still further object of the present invention is to provide a method for preparing the complex, which comprises the step of binding a physiologically active peptide, protein or other substance to the metal chelate forming peptide.

A still further object of the present invention is to provide a method for preparing the metal radio-nuclide labeled reagent, which comprises the step of coordinating a metal radionuclide to the metal chelate forming peptide or the above complex.

A still further object of the present invention is to provide a method for preparing a radiodiagnostic composition, which comprises the step of mixing the metal radionuclide-labeled reagent wherein any one of Tc-99m, In-111 and Ga-67 is coordinated, and a pharmaceutically acceptable carrier.

A still further object of the present invention is to provide a method for preparing a radiotherapeutic composition, which comprises the step of mixing a metal radionuclide-labeled reagent wherein any one of Y-90, Re-186 and Re-188 is coordinated, with a pharmaceutically acceptable carrier.

Throughout the specification, amino acids are expressed by either one letter abbreviation or three letters abbreviations. In an amino acid sequence, the N-terminus is shown at the left side, and the C-terminus at the right side. An abbreviation within the parenthesis after the amino acid abbreviation means a protecting group for the side chain, unless otherwise indicated. In the specification, D-amino acid residue is used to mean an amino acid residue in the D-form.

DETAILED DESCRIPTION OF THE INVENTION

The metal chelate forming peptide of the present invention comprises three amino acid residues having the amino acid sequence: X1-X2-Cys, wherein X1 represents an amino acid residue other than Cys residue; X2 represents an amino acid residue other than Cys residue and Pro residue; functional groups at the N-terminus, C-terminus and side chain may be optionally substituted with protecting groups; and each of the amino acid residue may be either D-form or L-form.

In the metal chelate forming peptide, Cys residue is unsuitable for the amino acid residue of X1 or X2, since Cys residue is not stable due to a tendency of the mercapto group therein to readily form intramolecular or intermolecular disulfide bonds. Where X2 is Pro residue, the chelating forming ability of the peptide is precluded so that the labeling efficiency of the peptide with a metal radionuclide is undesirably reduced. Except for the Cys and Pro residues, all other amino acid residues including D- and L-forms, hydrophobic amino acid residues, polar amino acid residues and chargeable amino acid residues (both acidic and basic) may be employed as the amino acid residues for X1 and X2.

The functional groups at the N-terminus, C-terminus and side chains of the metal chelate forming peptide may be substituted with protecting groups. Representative examples of such protecting groups are Boc, Fmoc and an ester group which are conventionally used for protecting an amino group and a carboxyl group.

In the amino acid sequence X1-X2 of the metal chelate forming peptide, it is advantageous to avoid the sequence of Asp residue and Gly residue adjacent with each other, Gly residue and Gly residue adjacent with each other, or Glu residue and Gly residue adjacent with each other. This is because a peptide having a carboxyl group at the side chain thereof such as Glu-Gly-Cys is known to be rapidly disintegrated in organs including kidney when administered to a mammal and be therefore unstable in a mammalian body. Further, where the amino acid sequence X1-X2 is Gly-Gly, the sequence has a large spatial latitude and is therefore readily folded in the peptide, resulting in that the peptide is reduced in the metal chelate forming ability.

The amino acid residue X1 is preferably an amino acid residue having a free amino group at the α-position thereof. Due to the presence of the free amino group at the a-position of X1, the metal chelating abilities of the metal chelate forming peptide and of the complex of the peptide with a physiologically active peptide, protein or other substance can be more enhanced. A particularly preferred embodiment is an amino acid residue X1 having a primary amino group (—NH$_2$) as the free amino group at the a-position thereof.

According to the present invention, preferred examples of the metal chelate forming peptide: X1-X2-Cys, are peptides having the following combinations of X1 and X2 sequence: Asp and Tyr residues, Asp and Lys residues, Tyr and Gly residues, Tyr and Tyr residues, Tyr and Lys residues, Lys and Gly residues, Lys and Tyr residues, and Lys and Lys residues.

It is preferred to choose the amino acid residues for X1 or X2 from hydrophobic amino acid residues such as Ala, Ile, Leu, Met, Phe and Val; polar amino acid residues such as Asn, Gln, His, Ser, Thr, Trp and Tyr; chargeable amino acids (both acidic and basic) such as Arg, Asp, Glu and Lys. By choosing suitably the amino acid residues for X1 and X2, the main route for the metabolite of the metal radionuclide-labeled reagent, which is prepared by binding the metal chelate forming peptide to a physiologically active peptide, protein or other substance followed by coordination with a metal radionuclide, can be controlled to localize either in the kidney or in the gastrointestinal tract (GI tract), when the reagent is administered to a mammal. Particularly when a specific amino acid residue is appropriately chosen for X1, the metabolite is selectively excreted from a desired organ. For example, when Asp or Lys residue is chosen as the amino acid residue for X1, the main route for metabolite excretion of the finally obtained metal radionuclide-labeled reagent can be selectively controlled to be localized in the kidney. When Tyr residue is chosen as the amino acid residue for X1, the main route of the metabolite excretion can be controlled to be localized in the GI tract.

The metal chelate forming peptide of the present invention is bound to a physiologically active peptide, protein or other substance to form a complex. When forming the complex, the metal chelate forming peptide may be bound to the physiologically active peptide or protein at the C-terminus or N-terminus thereof, or may be inserted into a site optionally selected between the C- and N-termini. The complex may also be formed by binding the N- or C-terminus of the metal chelate forming peptide to other physiologically active substances. When binding the metal chelate forming peptide to the physiologically active peptide, protein or other substance, they may be linked with each other through a spacer of one or more amino acid residues, functional group(s) or a cross-linking agent.

Typical examples of the physiologically active peptide, protein and other substance are interferon, cytokines such as tumor necrosis factor (TNF); various peptidic hormones and antibodies, complements, adhesion molecules and enzymes. The physiologically active peptide also includes active center sequence peptides which are selected from the sequences in antibodies or adhesion molecules. Additional examples of the physiologically active other substance are neurotransmitters such as dopamine, acetylcholine and serotonin; antibiotics such as streptomycin and cephalosporin; and prostaglandins.

As the physiologically active peptides, there are also preferably peptides having affinity for a focus site in a mammalian body, e.g., a peptide having affinity for a tumor site, a peptide having affinity for an inflammation and/or infection site, a peptide having affinity for a thrombus site, and a peptide having affinity for a cerebral disorders site. As the peptide having affinity for a focus site, known peptides may be employed as they are, without any modification.

An example of the peptide having affinity for a tumor site includes a peptide having the following amino acid sequence:

AREPPTRTFAYWGQG (SEQ ID NO:5)

In the above peptide, the amino acid sequence of EPPT is mainly attributed to the affinity for a tumor site. Therefore, so long as the EPPT sequence remains, any peptide modified by substitution, deletion or addition of amino acid residue(s) may also be preferably used as the peptide having affinity for a tumor site.

A representative example of the peptide having affinity for an inflammation and/or infection site is a peptide having the following amino acid sequence:

KTKPREQQYNSTYRVV (SEQ ID NO:6)

This peptide may be modified by substitution, deletion or addition of amino acid residue(s) so as not to impair its affinity for an inflammation and/or infection site.

The metal chelate forming peptide: X1-X2-Cys is bound to the aforesaid physiologically active peptide, protein or other substance, and the resulting complex then forms a chelate complex with a metal radionuclide. The chelate complex is advantageously utilized as an active agent in a diagnostic or therapeutic composition.

In the case of the complex of the metal chelate forming peptide with the physiologically active peptide, the complex may be readily synthesized according to a well known Boc method or Fmoc method, using an automated peptide synthesizer, e.g., Automatic Peptide Synthesizer of Applied Biosystems Inc. After the complex has been produced on a solid resin in the synthesizer, the protecting group is removed from the complex and at the same time, the complex is cleaved from the solid resin. Subsequently the complex may be purified by high performance liquid chromatography (HPLC) on a reversed phase column. The complex may also be prepared by liquid phase peptide synthesis, or may be collected from various animal sources.

The metal chelate forming peptide itself of the present invention comprising the three amino acid residues may also be synthesized by the same method as described above. For example, the peptide may be produced by binding cysteine or a protected derivative thereof to a solid phase resin, binding thereto the amino acid X2 or a protected derivative thereof and then the amino acid X1 or a protected derivative thereof, and finally cleaving the thus prepared peptide: X1-X2-Cys from the resin. Thus, the metal chelate forming peptide may be prepared in a simple manner.

When preparing the complex of the metal chelate forming peptide of the present invention with the physiologically active protein or other substance, the N-terminus or C-terminus amino acid residue in the metal chelate forming peptide is linked in a conventional manner to the terminus amino acid residue of the physiologically active protein or to the functional group of the physiologically active other substance. The binding or linkage is effected either via a spacer of one or more amino acid residues, functional group(s) or a crosslinking agent.

As stated hereinbefore, the metal chelate forming peptide of the present invention, which is one moiety of the complex, is preferably positioned in the complex at the N-terminus, and the α-amino group in the N-terminus amino acid residue of the metal chelate forming peptide in the complex preferably should remain free. Such a complex has a high chelate forming ability. The complex having a higher chelate forming ability can be obtained in a stable form, especially by selecting, as the N-terminus amino acid residue of the metal chelate forming peptide, an amino acid residue having a free primary amino group at the a-position thereof.

The metal radionuclide-labeled reagent, which is obtained by coordinating a metal radionuclide to the metal chelate forming peptide of the present invention or to the complex of the peptide with the physiologically active peptide, protein or other substance, preferably to the complex, may be used as a radiodiagnostic or radio-therapeutic agent. The metal radionuclide-labeled reagent may be prepared stably in vitro by dissolving the metal chelate forming peptide or the complex in physiological saline or in an aqueous buffer solution and then reacting the peptide or complex with a metal radio-nuclide.

For use in radiodiagnosis, the metal chelate forming peptide or the complex, preferably the complex, is bound to a metal radionuclide such as Tc-99m, In-111 or Ga-67, and the resulting metal radionuclide-labeled reagent is advantageously employed as a diagnostic agent.

For use in radiotherapeutics, the metal chelate forming peptide or the complex, preferably the complex, is bound to a metal radionuclide such as Y-90, Re-186 and Re-188, and the resulting metal radionuclide-labeled reagent is desirably employed as a radiotherapeutic agent.

Where the labeling is made with a metal radio-nuclide such as Tc-99m, Re-186 or Re-188, the labeled reagent may be prepared in a conventional manner by dissolving the metal chelate forming peptide or the complex of the peptide with the physiologically active peptide, protein or other substance in physiological saline or in an aqueous buffer solution, adding to the solution a reducing agent such as stannous chloride having an adequate reduction potential, and mixing the resulting mixture with a solution of sodium pertechnetate (Tc-99m) or a solution of sodium perrhenate (Re-186 and Re-188). In the case of In-111 labeling, the labeled reagent may be prepared by mixing the peptide or the complex with a weakly acidic aqueous solution containing In-111 ions. In the case of Ga-67 or Y-90 labeling, the labeled reagent may be prepared by adding the peptide or the complex to a weakly acidic or weakly alkaline aqueous solution containing Ga-67 ion or Y-90 ion.

Where the metal radionuclide-labeled reagent is provided for use in a radiodiagnostic or radiotherapeutic composition, the labeled regent prepared as described above may be purified by HPLC to remove impurities and unreacted pertechnetate ions, perrhenate ions, In-111 ion, Ga-67 ion and Y-90 ion, and then provided for use in the composition The radiolabeled reagent of the present invention may be mixed with pharmaceutically acceptable carriers to provide a radiodiagnostic composition or a radiotherapeutic composition. Typical examples of the carriers include a stabilizer such as ascorbic acid and p-aminobenzoic acid; a pH controlling agent such as an aqueous buffer solution; an excipient such as D-mannitol; a radiochemical purity enhancer such as citric acid, tartaric acid, malonic acid, sodium gluconate and sodium glucoheptonate. The radiodiagnostic or radiotherapeutic composition of the present invention may be also conveniently provided in a kit form ready for use, together with these carriers.

The radiodiagnostic or radiotherapeutic composition of the present invention, preferably comprising the metal radionuclide-labeled reagent obtained by labeling with a metal radionuclide the complex of the metal chelate forming peptide with the physiologically active peptide, protein or other substance, may be administered through a conventional parenteral route, e.g., by intravenous injection. The dose may vary depending on various conditions such as the body weight, age and disease conditions of a patient, radioactive imaging device used and the like. Taking these conditions into account, the radioactive dose which is considered as being appropriate for imaging and treatment is determined.

When administered to human, the dose of the diagnostic composition comprising the Tc-99m-labeled reagent is in a range of 37 MBq to 1110 mBg, preferably 185 MBq to 1110 MBq, in terms of the radioactivity of Tc-99m. In the case of the radiotherapeutic composition comprising the Re-186 or Re-188-labeled reagent, the dose is in a range of 37 MBq to 18500 MBq, preferably 370 MBq to 7400 MBq, in terms of the radioactivity. Where the therapeutic composition comprising the Y-90-labeled reagent is administered, the dose is in a range of 37 MBq to 3700 MBq, preferably 37 MBq to 1110 MBq, in terms of the radioactivity.

As stated hereinabove, the amino acid residues for X1 or X2 in the metal chelate forming peptide, X1-X2-Cys, of the present invention are chosen advantageously from hydrophobic amino acid residues such as Ala, Ile, Leu, Met, Phe and Val; polar amino acid residues such as Asn, Gln, His, Ser, Thr, Trp and Tyr; chargeable amino acids (both acidic and basic) such as Arg, Asp, Glu and Lys. By appropriately choosing the amino acid residue for X1 and X2, the main route for the metabolites of the metal radionuclide-labeled reagent can be controlled to localize either in the kidney or in the GI tract. That is, the main route for metabolite excretion can be controlled to be localized in the kidney, by selecting Asp or Lys residue for X1, and in the GI tract by selecting Tyr residue for X1. Such a selective localization results in rapid excretion of unnecessary metabolites at the site for diagnosis so that possible superfluous exposure to the patient can be minimized and, at the same time, the selective localization can eliminate noise at the background in imaging to achieve rapid imaging of the site for diagnosis. The metal chelate forming peptide of the present invention comprising the three amino acid residues is not physiologically active. Therefore, when the complex is formed, the peptide itself does not impair the activity inherently possessed by the physiologically active peptide, protein or other substance in the complex. This characteristic property is suitable for use in a radiodiagnostic or radiotherapeutic composition.

Hereinafter, the present invention is described more specifically with reference to the examples below, but is not construed to be limited thereto. In Examples 1 through 8, the complex disclosed in PCT/WO 9218534-A: KYCAREPP-TRTFAYWGQG (SEQ ID NO:2), which was obtained by binding a peptide containing EPPT having affinity for a tumor site to the metal chelate forming peptide (KYC) at the C-terminus thereof, was employed as a basic sequence. In the sequence, the two amino acid residues located at the N-terminus site were replaced by various amino acid residues, and Tc-99m labeling rates of the resulting complexes were determined to be used as an index for the metal chelating ability of each of the chelate forming peptides.

EXAMPLE 1

Synthesis of peptide containing KYC, D-KYC, DYC or YYC

A peptide containing KYC, D-KYC, DYC or YYC at the N-terminus site was synthesized on a pre-loaded resin according to a Fmoc method, using Peptide Synthesizer Model 431A (Applied Biosystems Inc.). The thus synthesized peptide was cleaved from the pre-loaded resin and deprotected by treatments comprising the steps of ice-cooling a mixture of 9.5 ml of trifluoroacetic acid (TFA), 0.5 ml of ethanedithiol (EDT), 1.0 ml of thioanisole, 0.75 g of phenol and 1.0 ml of purified water, adding 10 ml of the mixture to 0.1–0.2 g of the synthesized peptide and reacting them at room temperature for 1.5 hour. The obtained peptide was then purified by HPLC under the following conditions:

Column: YMC-Pack R & S-ODS-5-ST, 20×150 mm

Elution rate: 8 ml/min

Wavelength for detection: 230 nm

Eluent A: 0.1% TFA/purified water

Eluent B: 0.1% TFA/acetonitrile

Concentration gradient: 0 min (10% Eluent B)→15 mins (10% Eluent B)→75 mins (50% Eluent B)

The thus obtained main peak fractions were lyophilized and, the fractions having a purity of about 95% as determined by HPLC was subjected to amino acid analysis to determine the amino acid composition.

The purity was determined by HPLC under the following conditions.

Column: YMC-Pack ODS-A, 4.6×150 mm

Elution rate: 1 ml/min

Wavelength for detection: 215 nm

Eluent A: 0.1% TFA/purified water

Eluent B: 0.1% TFA/acetonitrile

Concentration gradient: 0 min (5% Eluent B)→30 mins (40% Eluent B)

The amino acid analysis was performed using PICO/TAG-TM Work Station (Waters Inc.). It was impossible to accurately measure Trp and Cys residues since Trp residue degraded by HCl decomposition and the mercapto group in Cys residue formed a disulfide bond. The obtained analytical data for the amino acid compositions of the peptides were expressed as the number of an amino acid residue per the peptide molecule, and the results are shown below. In the results, the numerical figure within parenthesis indicates the theoretical value for the number of an amino acid residue per the peptide molecule.

KYCAREPPTRTFAYWGQG (SEQ ID NO:2)=Glx:2.0 (2), Gly:2.4(2), Arg:2.0(2), Thr:2.3(2), Ala:1.9(2), Pro:2.2 (2), Tyr:2.1(2), Phe:0.9(1), Lys:0.9(1), Cys:–(1), Trp:–(1).

D-KYCAREPPTRTFAYWG-D-QG=Glx:2.0(2), Gly:2.2 (2), Arg:1.9(2), Thr:2.0(2), Ala:2.1(2), Pro:2.1(2), Tyr:1.8 (2), Phe:1.1(1), Lys:1.0(1), Cys:–(1), Trp:–(1).

DYCAREPPTRTFAYWGQG (SEQ ID NO:7)=Asp:1.0 (1), Glx:2.0(2), Gly:2.1(2), Arg:2.0(2), Thr:1.9(2), Ala:2.0 (2), Pro:2.0(2), Tyr:2.1(2), Phe:1.0(1), Cys:–(1), Trp:–(1).

YYCAREPPTRTFAYWGQG (SEQ ID NO:8)=Glx:2.0 (2), Gly:2.1(2), Arg:2.0(2), Thr:1.9(2), Ala:2.0(2), Pro:2.1 (2), Tyr:2.9(3), Phe:1.1(1), Lys:1.0(1), Cys:–(1), TRP:–(1).

EXAMPLE 2

Radiolabeling of the peptide containing KYC, D-KYC, DYC or YYC with Tc-99m

In a lyophilized vial charged with a mixture of 40.3 μmol/300 μl of glucoheptonate and 130 nmol/50 μl of stannous chloride solution, 1.1 to 1.5 GBq of sodium pertechnetate (Tc-99m) solution was added to make the whole volume 1.0 ml. The reaction was carried out at room temperature for 30 minutes while occasionally tumbling the vial. An aliquot of the reaction mixture was subjected to electrophoresis on cellulose acetate membrane to confirm whether the radiolabeling of glucoheptonate with Tc-99m reached 95% or more. Then, the four peptides obtained in Example 1 were diluted to have various concentrations in the range from 0.25 to 12.5 nmol/200 μl. Each of those dilutions was mixed with 200 μl of Tc-99m-labeled glucoheptonate solution to react them at room temperature for 60 minutes. The reaction mixture was allowed to be cooled. An aliquot of the reaction mixture was examined for a radiolabeling rate with Tc-99m by HPLC under the following conditions.

Column: Millipore puresil 5 μm C18, 4.6×150 mm

Elution rate: 1 ml/min

Wavelength for detection: 220 nm

Radioactivity detector: NaI single channel analyzer

Eluent A: 0.1% TFA/purified water

Eluent B: 0.1% TFA/acetonitrile

Concentration gradient: 0 min (10% Eluent B)→5 mins (10% Eluent B)→35 mins (50% Eluent B)→45 mins (75% Eluent B)

The obtained radiolabeling rates of the four Tc-99m-labeled peptides are shown in Table 1. The results in Table 1 demonstrate that 90% or more Tc-99m radiolabeling was achieved even when peptides having a low concentration of 25 μg/ml were radiolabeled at a room temperature.

EXAMPLE 3

Metal chelating ability of Ac-KYCAREPPTRTFAYWGOG-NH$_2$ (SEQ ID NO:$_2$) and KYCAREPPTRTFAYWGOG-NH$_2$ (SEQ ID NO:2)

The two following peptides were evaluated for the metal chelating ability.

Ac-KYCAREPPTRTFAYWGQG-NH$_2$(SEQ ID NO:2):
  wherein the α-amino group of the N-terminus lysine (K) residue was acetylated, and the terminus carboxyl group was amidated (NH$_2$).

KYCAREPPTRTFAYWGQG-NH$_2$(SEQ ID NO:2):
  wherein the α-amino group of the N-terminus lysine (K) residue was free, and the terminus carboxyl group was amidated (NH$_2$).

The two peptide were examined for the metal chelating ability with a metal radionuclide. That is, the metal chelating abilities were compared in the two peptide, one peptide wherein the a-amino group in the N-terminus amino acid residue remains free (not protected), and other peptide wherein the α-amino group is acetylated.

Radiolabeling with Tc-99m and purification of the peptides were carried out in a manner similar to Example 2, except for using amidated resin (PAL resin, Millipore) instead of the pre-loaded resin.

The obtained analytical data for the amino acid compositions of the peptides were expressed as the number of an amino acid residue per the peptide molecule, and the results are shown below. In the results, the numerical figure within parenthesis indicates the theoretical value for the number of an amino acid residue per the peptide molecule.

Ac-KYCAREPPTRTFAYWGQG-NH$_2$ (SEQ ID NO:2)= Glx:2.1(2), Gly:2.5(2), Arg:2.0(2), Thr:1.5(2), Ala:1.8(2), Pro:2.1(2), Tyr:1.9(2), Phe:1.2(1), Lys:1.0(1), Cys:–(1), Trp:–(1).

KYCAREPPTRTFAYWGQG-NH$_2$ (SEQ ID NO:2)= Glx:2.1(2), Gly:2.2(2), Arg:2.1(2), Thr:1.6(2), Ala:1.9(2), Pro:2.1(2), Tyr:1.7(2), Phe:1.3(1), Lys:1.0(1), Cys:–(1), Trp:–(1).

Figure 1:
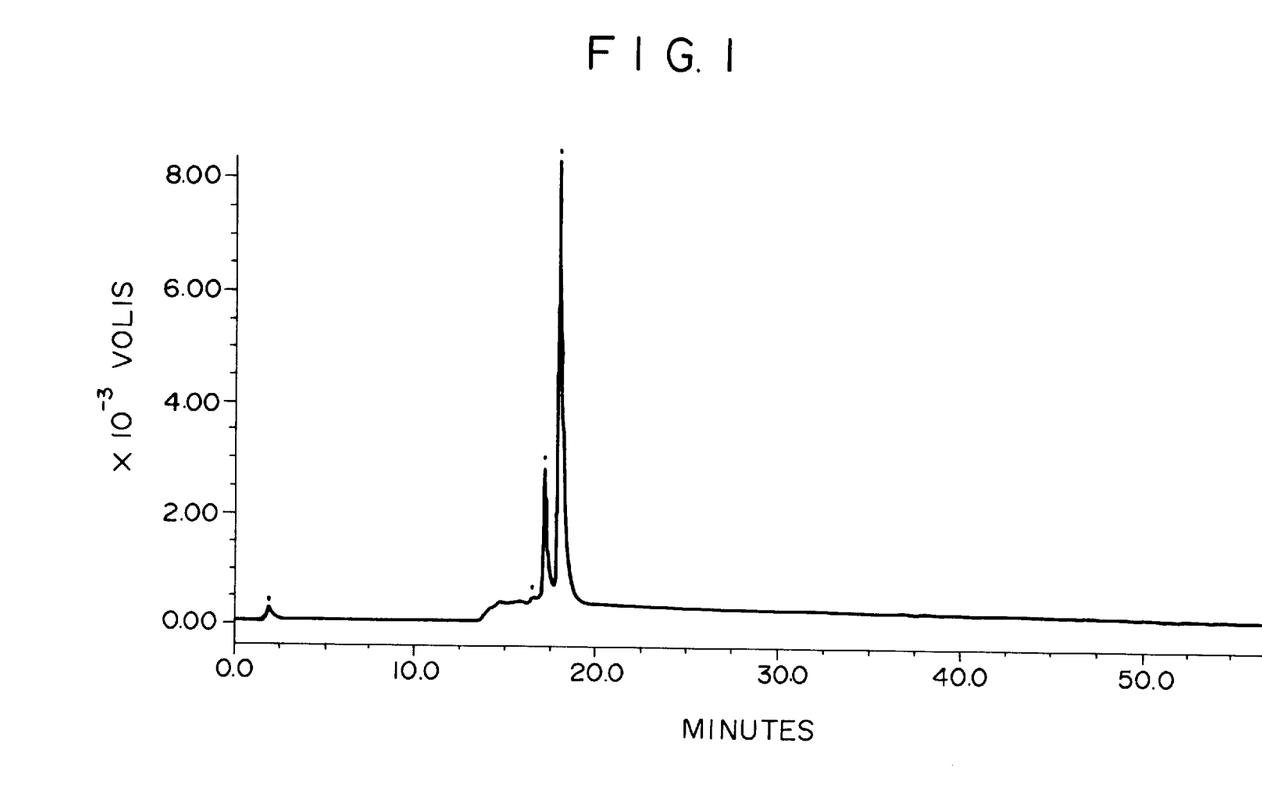
FIG. 1 is a radioactive HPLC profile of Ac-KYCAREPPTRTFAYWGQG-NH$_2$ (SEQ ID NO:2) labeled with Tc-99m.
Figure 2:
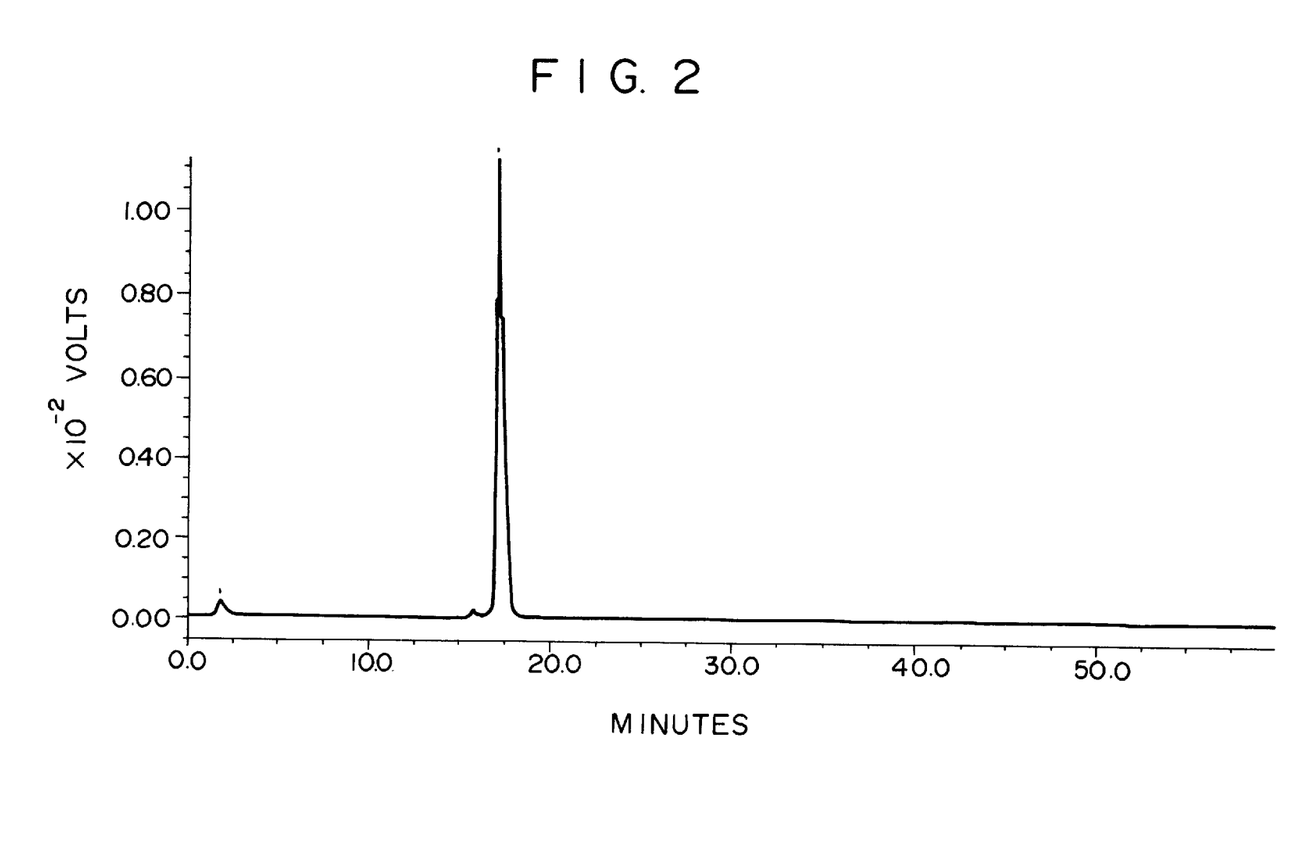
FIG. 2 is a radioactive HPLC profile of KYCAREPPTRTFAYWGQG-NH$_2$ (SEQ ID NO:2) labeled with Tc-99m.

The results of the labeled peptides by HPLC analysis are shown in FIGS. 1 and 2. The peptide, which retained at the N-terminus the amino acid residue having the non-acetylated free α-amino group, showed a single radioactivity

TABLE 1

Radiolabeling rate (%) of the peptides containing KYC, D-KYC, DYC and YYC with Tc-99m (n = 3, mean ± standard deviation)

| Metal chelate forming peptide | Concentration of Sample | | | | |
|---|---|---|---|---|---|
| | 100 μg/ml | 50 μg/ml | 25 μg/ml | 10 μg/ml | 5 μg/ml |
| KYC | 97.8 ± 0.69 | 96.4 ± 0.32 | 92.2 ± 1.39 | 79.6 ± 6.62 | 39.1 ± 1.59 |
| D-KYC | 99.8 ± 0.11 | — | 97.7 ± 0.33 | — | 10.5 ± 0.43 |
| DYC | 100 ± 0.00 | 98.1 ± 0.45 | 90.6 ± 1.95 | 88.9 ± 2.82 | 28.7 ± 6.34 |
| YYC | 99.4 ± 0.39 | 97.9 ± 0.57 | 93.4 ± 2.51 | 79.4 ± 1.71 | 29.2 ± 17.2 | peak (retention time: 17.08 mins, as shown in FIG. 2). On the other hand, the other peptide containing at the N-terminus the amino acid residue having the acetylated α-amino group showed two radioactivity peaks (retention times: 17.19 mins and 18.01 mins, as shown in FIG. 1). The two peptides were proved to have the metal chelating ability with a metal radionuclide such as Tc-99m.

However, the peptide containing at the N-terminus the amino acid residue having the acetylated α-amino group was considered not to be excellent in the structural stability and labeling purity, because the radioactivity profile showed the two radioactivity peaks. On the other hand, the other peptide showed the single radioactivity peak, suggesting that a peptide which contains the N-terminus amino acid residue having a free and primary amino group as the a-amino group is highly excellent both in the structural stability and labeling purity.

EXAMPLE 4

Synthesis of the peptide containing KGC, KPC, D-KPC or YKC

The peptide containing KGC, KPC, D-KPC or YKC was synthesized and purified in a manner similar to Example 1. The obtained analytical data for the amino acid compositions of the peptides were expressed as the number of an amino acid residue per the peptide molecule, and the results are shown below. In the results, the numerical figure within parenthesis indicates the theoretical value for the number of an amino acid residue per the peptide molecule.

KGCAREPPTRTFAYWGQG (SEQ ID NO:9)=Glx:2.0 (2), Gly:3.2(3), Arg:2.1(2), Thr:1.8(2), Ala:1.8(2), Pro:2.0 (2), Tyr:1.0(1), Phe:1.1(1), Lys:1.0(1), Cys:–(1), Trp:–(1).

KPCAREPPTRTFAYWGQG (SEQ ID NO:10)=Glx:2.0 (2), Gly:2.1(2), Arg:2.0(2), Thr:2.0(2), Ala:1.9(2), Pro:3.1 (3), Tyr:1.0(1), Phe:1.0(1), Lys:1.0(1), Cys:–(1), Trp:–(1).

D-KPCAREPPTRTFAYWGQG=Glx:1.9(2), Gly:2.3(2), Arg:1.9(2), Thr:1.8(2), Ala:1.9(2), Pro:3.4(3), Tyr:1.0(1), Phe:1.1(1), Lys:0.7(1), Cys:–(1), Trp:–(1).

YKCAREPPTRTFAYWGQG (SEQ ID NO:11)=Glx:2.0 (2), Gly:2.2(2), Arg:2.1(2), Thr:1.8(2), Ala:1.8(2), Pro:2.0 (2), Tyr:2.0(2), Phe:1.1(1), Lys:1.0(1), Cys:–(1), Trp:–(1).

EXAMPLE 5

Radiolabeling of the peptide containing KGC, YKC, KPC or D-KPC with Tc-99m

The four peptides obtained in Example 4 were labeled with Tc-99m in a manner similar to Example 2. The radiolabeling rates of the resulting Tc-99m-labeled peptides are shown in Table 2, together with that of the Tc-99m-labeled peptide containing KYC obtained in Example 2. Compared with the samples having a concentration of 100 μg/ml, the results in Table 2 reveal that the peptide having Tyr residue, Gly residue or Lys residue as X2 achieved 98% or more radiolabeling rate, whereas the peptide having Pro residue as X2 merely achieved 50 to 70% radiolabeling rate.

TABLE 2

Radiolabeling rate (%) of the peptides containing KYC, KGC, YKC, KPC and D-KPC and Tc-99m
(n = 3, mean ± standard deviation)

| Metal chelate forming peptide | Concentration of Sample | | |
|---|---|---|---|
|  | 100 μg/ml | 50 μg/ml | 25 μg/ml |
| KYC | 97.8 ± 0.69 | 96.4 ± 0.32 | 92.2 ± 1.39 |
| KGC | 98.2 ± 0.11 | 93.2 ± 1.77 | 91.9 ± 4.73 |
| YKC* | 98.1 | 97.6 | 96.9 |
| KPC | 53.6 ± 0.81 | 51.0 ± 0.13 | — |
| D-KPC | 69.1 ± 1.86 | 67.1 ± 0.06 | — |

*n = 1

EXAMPLE 6

Stability of Tc-99m-labeled KYCAREPPTRTFAYWGQG (SEQ ID NO:2)

Figure 3:
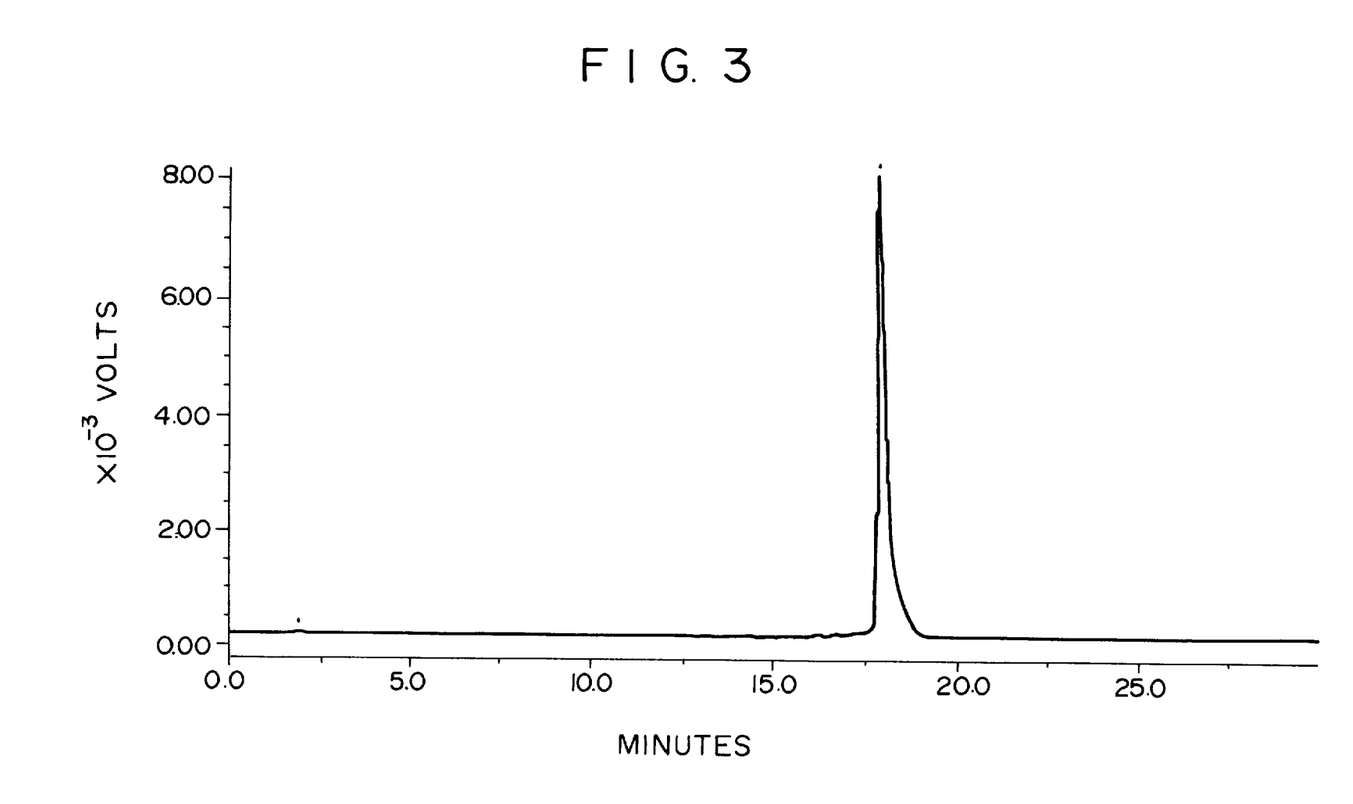
FIG. 3 is a radioactive HPLC profile of Tc-99m-KYCAREPPTRTFAYWGQG (SEQ ID NO:2) mixed with DTPA in 1000-fold amount.

Tc-99m-labeled KYCAREPPTRTFAYWGQG (SEQ ID NO:2) was prepared according to the methods in Examples 1 and 2. The labeled peptide was mixed with DTPA solution in 1000-fold molar amount, and the mixture was allowed to stand for an hour at room temperature. The labeled peptide was examined for the chelate stability in terms of transchelation rate of Tc-99m into DTPA. The transchelation rate was measured by HPLC as described in Example 1, and the obtained results are shown in FIG. 3. As shown in FIG. 3, it was confirmed that even when DTPA was added in 1000-fold molar amount, any radioactivity peak other than the single peak (retention time: 17.08 mins) was not observed, and Tc-99m-KYC therefore remained stably in the labeled peptide.

EXAMPLE 7

Biodistribution of Tc-99m-labeled peptide containing KYC, DYC or YYC

SD strain rats (Sprague-Dawley) weighing 140 to 200 g were anesthetized with sodium thiopentobarbital. The three Tc-99m-labeled peptides, Tc-99m-KYCAREPPTRTFAYWGQG (SEQ ID NO:2), Tc-99m-DYCAREPPTRTFAYWGQG (SEQ ID NO:7) and Tc-99m-YYCAREPPTRTFAYWGQG (SEQ ID NO:8) obtained in Example 2, were intravenously administered to the rats in the tail vein at a dose of 3.0 to 3.7 MBq. After 5, 30, 60 and 180 minutes, the rats were sacrificed to be subjected to a radioactive distribution analysis in each organ using NaI single channel analyzer. The results are shown in Tables 3, 4 and 5.

TABLE 3

Biodistribution of Tc-99m-DYC peptide
(upper value: % ID/organ, lower value: % ID/g)
(n = 3, mean ± standard deviation)

| Organ | After 5 min | After 30 min | After 60 min | After 180 min |
|---|---|---|---|---|
| Liver | 2.31 ± 0.06 | 1.20 ± 0.11 | 0.56 ± 0.17 | 0.16 ± 0.02 |
|  | 0.33 ± 0.05 | 0.19 ± 0.01 | 0.10 ± 0.03 | 0.03 ± 0.00 |
| Small intestine | 2.42 ± 0.18 | 2.83 ± 0.53 | 4.18 ± 1.35 | 4.54 ± 0.59 |
|  | 0.33 ± 0.03 | 0.44 ± 0.10 | 0.66 ± 0.14 | 0.85 ± 0.12 |
| Large intestine | 1.53 ± 0.21 | 0.58 ± 0.16 | 0.28 ± 0.06 | 0.26 ± 0.03 |

TABLE 3-continued

Biodistribution of Tc-99m-DYC peptide
(upper value: % ID/organ, lower value: % ID/g)
(n = 3, mean ± standard deviation)

| Organ | After 5 min | After 30 min | After 60 min | After 180 min |
|---|---|---|---|---|
| | 0.21 ± 0.02 | 0.09 ± 0.03 | 0.04 ± 0.01 | 0.03 ± 0.01 |
| Stomach | 0.83 ± 0.06 | 0.71 ± 0.09 | 0.67 ± 0.07 | 0.60 ± 0.20 |
| | 0.20 ± 0.03 | 0.16 ± 0.01 | 0.13 ± 0.01 | 0.16 ± 0.06 |
| Spleen | 0.15 ± 0.00 | 0.05 ± 0.01 | 0.02 ± 0.01 | 0.01 ± 0.00 |
| | 0.32 ± 0.03 | 0.14 ± 0.03 | 0.07 ± 0.02 | 0.02 ± 0.00 |
| Lung | 1.14 ± 0.12 | 0.47 ± 0.03 | 0.22 ± 0.03 | 0.07 ± 0.01 |
| | 1.16 ± 0.04 | 0.52 ± 0.01 | 0.28 ± 0.02 | 0.09 ± 0.02 |
| Heart | 0.33 ± 0.03 | 0.10 ± 0.01 | 0.04 ± 0.01 | 0.00 ± 0.00 |
| | 0.53 ± 0.06 | 0.17 ± 0.02 | 0.07 ± 0.01 | 0.01 ± 0.00 |
| Kidney | 7.60 ± 0.90 | 3.93 ± 0.07 | 2.09 ± 0.53 | 0.69 ± 0.29 |
| | 5.28 ± 0.35 | 2.87 ± 0.03 | 1.67 ± 0.48 | 0.58 ± 0.25 |
| Whole blood | 16.55 ± 0.89 | 4.78 ± 0.56 | 2.29 ± 1.01 | 0.29 ± 0.18 |
| | 1.51 ± 0.08 | 0.46 ± 0.06 | 0.24 ± 0.12 | 0.03 ± 0.02 |
| Carcass | 54.28 ± 3.30 | 22.95 ± 2.87 | 8.24 ± 2.44 | 3.18 ± 2.67 |
| | 0.43 ± 0.03 | 0.19 ± 0.02 | 0.07 ± 0.02 | 0.03 ± 0.02 |
| Urine | 19.15 ± 2.74 | 64.22 ± 3.06 | 82.35 ± 4.19 | 90.32 ± 3.59 |

TABLE 4

Biodistribution of Tc-99m-KYC peptide
(upper value: % ID/organ, lower value: % ID/g)
(n = 3, mean ± standard deviation)

| Organ | After 5 min | After 30 min | After 60 min | After 180 min |
|---|---|---|---|---|
| Liver | 3.63 ± 1.75 | 2.88 ± 0.56 | 1.77 ± 0.68 | 0.99 ± 0.50 |
| | 0.58 ± 0.28 | 0.43 ± 0.05 | 0.27 ± 0.12 | 0.15 ± 0.07 |
| Small intestine | 2.75 ± 0.78 | 3.14 ± 0.65 | 3.69 ± 0.16 | 2.09 ± 0.48 |
| | 0.40 ± 0.09 | 0.48 ± 0.12 | 0.53 ± 0.02 | 0.29 ± 0.09 |
| Large intestine | 1.63 ± 0.38 | 0.56 ± 0.08 | 0.24 ± 0.01 | 3.55 ± 1.22 |
| | 0.23 ± 0.03 | 0.10 ± 0.03 | 0.04 ± 0.00 | 0.51 ± 0.16 |
| Stomach | 0.65 ± 0.22 | 0.45 ± 0.14 | 0.36 ± 0.23 | 0.06 ± 0.04 |
| | 0.27 ± 0.06 | 0.16 ± 0.05 | 0.13 ± 0.08 | 0.02 ± 0.01 |
| Spleen | 0.33 ± 0.20 | 0.14 ± 0.06 | 0.09 ± 0.05 | 0.06 ± 0.04 |
| | 0.82 ± 0.51 | 0.34 ± 0.15 | 0.20 ± 0.12 | 0.16 ± 0.10 |
| Lung | 1.09 ± 0.52 | 0.45 ± 0.09 | 0.19 ± 0.08 | 0.07 ± 0.04 |
| | 1.10 ± 0.45 | 0.48 ± 0.07 | 0.22 ± 0.10 | 0.08 ± 0.04 |
| Heart | 0.29 ± 0.08 | 0.12 ± 0.01 | 0.04 ± 0.01 | 0.01 ± 0.00 |
| | 0.49 ± 0.11 | 0.20 ± 0.02 | 0.06 ± 0.01 | 0.01 ± 0.00 |
| Kidney | 9.65 ± 1.99 | 6.80 ± 0.84 | 5.22 ± 0.93 | 4.75 ± 1.08 |
| | 8.06 ± 2.66 | 5.36 ± 0.31 | 3.97 ± 0.64 | 3.69 ± 0.54 |
| Whole blood | 17.38 ± 1.58 | 6.85 ± 1.68 | 2.06 ± 0.33 | 0.37 ± 0.14 |
| | 1.56 ± 0.07 | 0.62 ± 0.14 | 0.18 ± 0.03 | 0.03 ± 0.01 |
| Carcass | 50.31 ± 2.82 | 25.57 ± 2.55 | 8.39 ± 1.12 | 2.20 ± 1.51 |
| | 0.39 ± 0.03 | 0.20 ± 0.03 | 0.18 ± 0.03 | 0.02 ± 0.01 |
| Urine | 19.46 ± 8.85 | 55.55 ± 4.91 | 78.81 ± 0.99 | 86.01 ± 3.07 |

TABLE 5

Biodistribution of Tc-99m-YYC peptide
(upper value: % ID/organ, lower value: % ID/g)
(n = 3, mean ± standard deviation)

| Organ | After 5 min | After 30 min | After 60 min | After 180 min |
|---|---|---|---|---|
| Liver | 7.46 ± 0.52 | 3.97 ± 0.23 | 1.99 ± 0.37 | 0.59 ± 0.06 |
| | 1.05 ± 0.08 | 0.56 ± 0.03 | 0.28 ± 0.06 | 0.09 ± 0.01 |
| Small intestine | 4.23 ± 0.63 | 25.03 ± 5.42 | 37.35 ± 3.38 | 23.28 ± 4.42 |
| | 0.50 ± 0.05 | 3.00 ± 0.88 | 4.81 ± 0.70 | 3.00 ± 0.41 |
| Large intestine | 1.70 ± 0.25 | 0.49 ± 0.18 | 0.19 ± 0.05 | 20.66 ± 6.82 |
| | 0.22 ± 0.02 | 0.07 ± 0.01 | 0.03 ± 0.01 | 2.12 ± 0.72 |
| Stomach | 0.87 ± 0.22 | 0.61 ± 0.67 | 0.18 ± 0.08 | 0.04 ± 0.00 |
| | 0.13 ± 0.01 | 0.09 ± 0.09 | 0.03 ± 0.02 | 0.10 ± 0.00 |
| Spleen | 0.30 ± 0.04 | 0.15 ± 0.01 | 0.11 ± 0.02 | 0.03 ± 0.01 |
| | 0.70 ± 0.00 | 0.36 ± 0.07 | 0.25 ± 0.06 | 0.06 ± 0.01 |

TABLE 5-continued

Biodistribution of Tc-99m-YYC peptide
(upper value: % ID/organ, lower value: % ID/g)
(n = 3, mean ± standard deviation)

| Organ | After 5 min | After 30 min | After 60 min | After 180 min |
|---|---|---|---|---|
| Lung | 2.82 ± 0.27 | 1.34 ± 0.10 | 0.99 ± 0.21 | 0.36 ± 0.06 |
| | 3.20 ± 0.37 | 1.48 ± 0.31 | 1.02 ± 0.18 | 0.37 ± 0.07 |
| Heart | 0.33 ± 0.02 | 0.09 ± 0.02 | 0.04 ± 0.01 | 0.00 ± 0.00 |
| | 0.59 ± 0.05 | 0.15 ± 0.03 | 0.06 ± 0.03 | 0.01 ± 0.00 |
| Kidney | 5.76 ± 0.64 | 2.38 ± 0.51 | 1.86 ± 0.79 | 0.87 ± 0.73 |
| | 4.94 ± 0.79 | 1.87 ± 0.27 | 1.40 ± 0.60 | 0.68 ± 0.62 |
| Whole blood | 17.63 ± 2.89 | 4.65 ± 1.30 | 1.61 ± 0.95 | 0.10 ± 0.04 |
| | 1.63 ± 0.33 | 0.41 ± 0.09 | 0.14 ± 0.08 | 0.01 ± 0.00 |
| Carcass | 54.57 ± 2.67 | 22.78 ± 4.44 | 8.46 ± 2.68 | 2.08 ± 1.87 |
| | 0.44 ± 0.03 | 0.17 ± 0.03 | 0.06 ± 0.02 | 0.02 ± 0.01 |
| Urine | 11.63 ± 3.99 | 40.29 ± 1.70 | 47.88 ± 1.42 | 52.01 ± 3.89 |

The results in Tables 3, 4 and 5 demonstrate that the in vivo distribution of the Tc-99m-labeled peptides in normal rats was remarkably changed with only the difference in the amino acid residue of X1 between the labeled peptides. Especially when the labeled peptide had Asp residue or Lys residue as X1, the peptide was excreted rapidly from the kidney, and was excreted at 82% radioactivity to urine even 60 minutes after administered. In contrast, when the peptide had Tyr residue as X1, the peptide accumulated at 37% radioactivity in the small intestine 60 minutes after administered. Thereafter, the peptide was excreted to feces through the GI tract.

EXAMPLE 8

Imaging of tumor using Tc-99m-
KYCAREPPTRTNAYWGQG (SEQ ID NO:3)

A peptide containing KYC at the N-terminus KYCAREPPTRTNAYWGQG (SEQ ID NO:3) was synthesized and purified according to the method in Example 1. Radiolabeling with Tc-99m was performed in the same way as in Example 2 followed by HPLC analysis. The obtained analytical data for the amino acid composition of the peptide: KYCAREPPTRTNAYWGQG (SEQ ID NO:3) were expressed as the number of an amino acid residue per the peptide molecule, and the results are shown below. In the results, the numerical figure within parenthesis indicates the theoretical value for the number of an amino acid residue per the peptide molecule.

KYCAREPPTRTNAYWGQG (SEQ ID NO:3)=Asn:1.1 (1), Glx:2.0(2), Gly:2.1(2), Arg:1.9(2), Thr:2.0(2), Ala:1.9 (2), Pro:2.1(2), Tyr:2.0(2), Lys:0.9(1), Cys:–(1), Trp:–(1).

Figure 4:
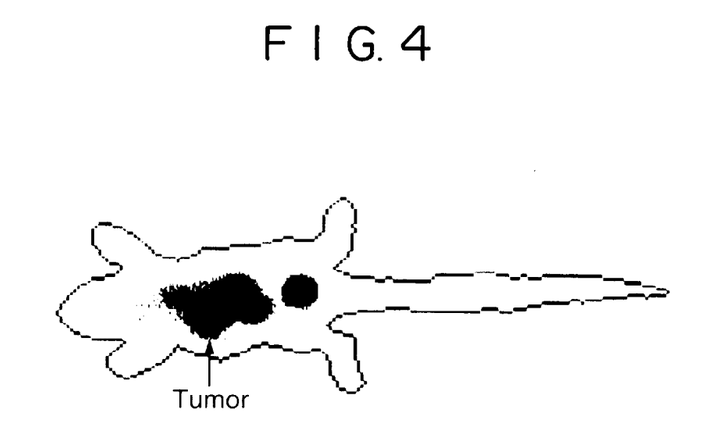
FIG. 4 is a photograph showing a scintigram of the whole body of a model mouse with tumor, taken 5 minutes after Tc-99m-KYCAREPPTRTNAYWGQG (SEQ ID NO:3) was administered to the mouse.
Figure 5:
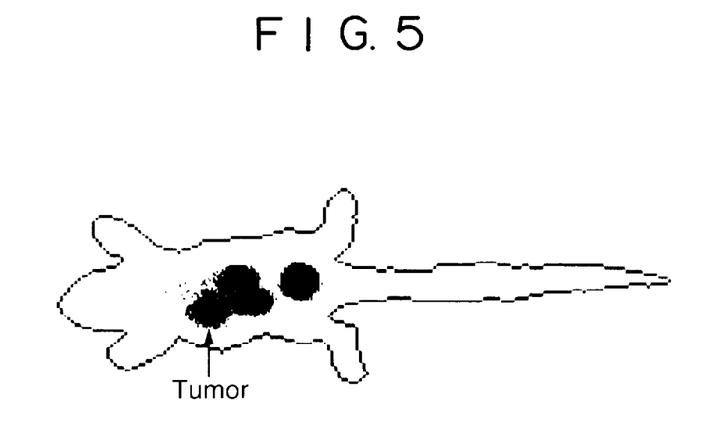
FIG. 5 is a photograph showing a scintigram of the whole body of a model mouse with tumor, taken 20 minutes after Tc-99m-KYCAREPPTRTNAYWGQG (SEQ ID NO:3) was administered to the mouse.

Tumor cells HEp2 ($5 \times 10^6$ cells, Human Epidermoid Carcinoma; ATCC No. CCL 23) were suspended in 1.0 ml of medium (Minimum essential medium (Eagle's) with Earle's BSS, 90% fetal bovine serum, 10%), and 100 µl of the suspension was subcutaneously injected to BALB/C nude mouse (6 weeks age) at the body side. Two weeks after the injection, the mouse wherein the implanted tumor grew to about 0.3 g seize was anesthetized with sodium thiopentobarbital, and injected by the Tc-99m-labeled peptide at the tail vein at a dose of 35 to 40 MBq. Five and 20 minutes after the injection, the animal was imaged with a gamma camera. The obtained results are shown in FIGS. 4 and 5.

Immediately after the imaging, the animal was sacrificed and examined for the distribution of the radioactivity in each organ using NaI single channel analyzer to determine a ratio of the radioactivity in tumor site to the radioactivity in muscle site (T/B ratio). Twenty minutes after the Tc-99m-labeled peptide was injected, the T/B ratio showed 4.50±0.71 (n=3, mean±standard deviation), and the tumor site was clearly imaged. Such results demonstrate that the metal chelate forming peptide KYC of the present invention is useful for stably radiolabeling with Tc-99m the peptide having affinity for tumor site: AREPPTRTFAYWGQG (SEQ ID NO:5) (PCT/WO 9218534-A) in such a way that the pharmacological activity of the peptide was retained.

EXAMPLE 9

Preparation of Tc-99m-KYCGGKTKPREOOYNSTYRVV-NH$_2$(SEQ ID NO:4)

Peptide: KYCGGKTKPREQQYNSTYRWV-NH$_2$ (SEQ ID NO:4) was synthesized and purified in the same way as in Example 1, except for using amidated resin (PAL resin, Millipore) instead of the pre-loaded resin. Then, the synthesized peptide was labeled with Tc-99m and analyzed by HPLC in the same way as in Example 2. The obtained analytical data for the amino acid compositions of the peptides were expressed as the number of an amino acid residue per the peptide molecule, and the results are shown below. In the results, the numerical figure within parenthesis indicates the theoretical value for the number of an amino acid residue per the peptide molecule.

KYCGGKTKPREQQYNSTYRVV-NH$_2$ (SEQ ID NO:4) =Asp:1.1(1), Glx:3.0(3), Ser:0.9(1), Gly:2.1(2), Arg:2.0(2), Thr:2.2(2), Pro:1.0(1), Tyr:3.2(3), Val:1.5(2), Lys:3.0(3), Cys:–(1).

In a lyophilized vial charged with a mixture of 40.3 µmol/300 µl of glucoheptonate and 130 nmol/50 µl of stannous chloride solution, 1.5 to 1.8 GBq of sodium pertechnetate (Tc-99m) solution was added to make the whole volume 1.0 ml. The reaction was carried out at room temperature for 30 minutes while occasionally tumbling the vial. An aliquot of the reaction mixture was subjected to electrophoresis on cellulose acetate membrane to confirm whether the radiolabeling of glucoheptonate with Tc-99m reached 95% or more. Then, 40 nmol/500 µl of the peptide was mixed with 500 µl of Tc-99m-labeled glucoheptonate solution. The reaction was carried out for 20 minutes on a boiling water bath. The reaction mixture was then allowed to be cooled. An aliquot of the reaction mixture was subjected to TLC (TLC plate: ODS, developing solvent: 0.1% TFA/60% acetonitrile/purified water) to determine the radiolabeling rate with Tc-99m. As a result, the radiolabeling rate of the peptide was 90%.

EXAMPLE 10

Imaging of inflammation using Tc-99m-KYCGGKTKPREOOYNSTYRVV-NH$_2$ (SEQ ID NO:4)

Figure 6:
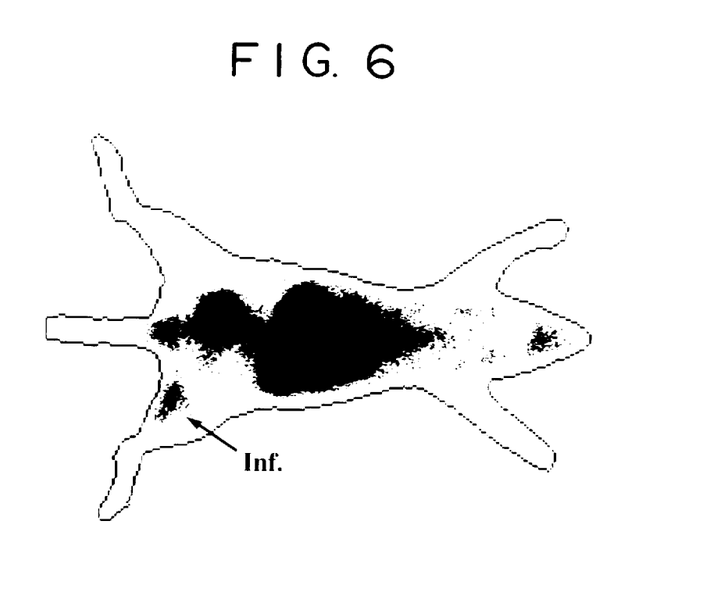
FIG. 6 is a photograph showing a scintigram of the whole body of a model rat with inflammation, taken 30 minutes after Tc-99m-KYCGGKTKPREQQYNSTYRVV-NH$_2$ (SEQ ID NO:4) was administered to the rat.
Figure 7:
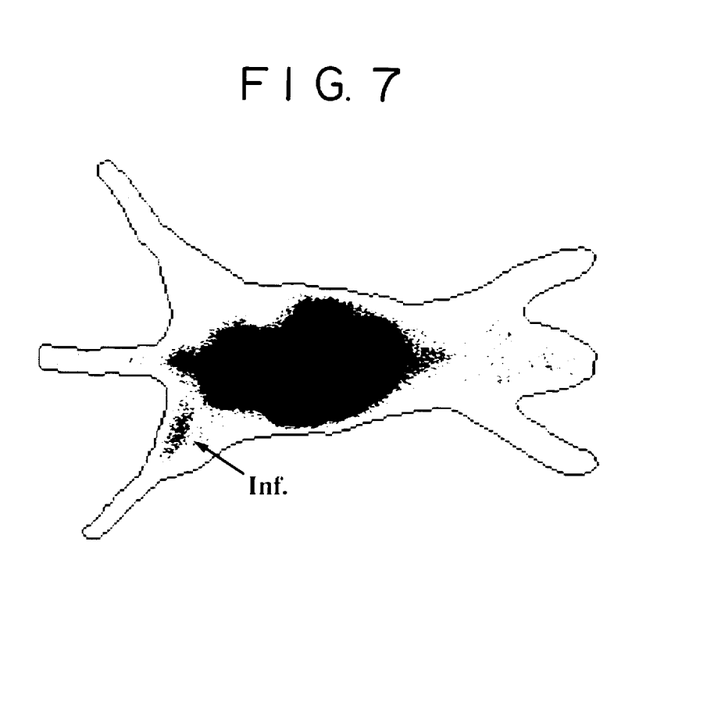
FIG. 7 is a photograph showing a scintigram of the whole body of a model rat with inflammation, taken 120 minutes after Tc-99m-KYCGGKTKPREQQYNSTYRVV-NH$_2$ (SEQ ID. NO:4) was administered to the rat.

*Staphylococcus aureus* $10^8$ cells were suspended in 1 ml of physiological saline, and 100 µl of the suspension was intramuscularly administered to SD rats weighing about 220 g at the right calf. After 24 hours, the rat wherein inflammation was clearly observed was anesthetized with sodium thiopentobarbital and injected by the Tc-99m labeled peptide: KYCGGKTKPREQQYNSTYRVV-NH$_2$ (SEQ ID NO:4) obtained in Example 9 at the tail vein at a dose of 37 to 74 MBq. Thirty and 120 minutes after the peptide was injected, the animal was imaged with a gamma camera. The obtained results are shown in FIGS. 6 and 7. Regions of interest were selected from the obtained image to determine a ratio T/B of the radioactivity in inflammation site (T) to the radioactivity in normal site (B). The T/B ratio showed 3.26±0.18 (n=6, mean±standard deviation), and the inflammation site was clearly imaged. The obtained results demonstrate that Tc-99m-KYC of the present invention is useful for stably radiolabeling with Tc-99m the peptide having affinity for inflammation: GGKTKPREQQYNSTYRWV-NH$_2$ (SEQ ID NO:12) in such a way that the pharmacological activity of the peptide was retained.

As described in detail hereinbefore, the metal chelate forming peptide of the present invention comprising the specific three amino acids of X1-X2-Cys is advantageous in that the peptide enables easy handling without any particular consideration on the undesired intramolecular and intermolecular disulfide bond formation in the prior art; the peptide may be bound to a physiologically active peptide, protein or other substance to form a complex without damaging the activity of the physiologically active peptide and the like; the peptide enables a stable formation of a radioactive chelate complex with a metal radionuclide such as Tc-99m both in vitro and in vivo; and the peptide can provide the radioactivity that does not cause non-specific accumulation in distribution in vivo of the finally produced labeled reagent, enabling to design a metabolite route for excretion of the labeled reagent as needed or depending upon purpose.

What is claimed is:

1. A metal chelate forming peptide having an amino acid sequence represented by:

X1-X2-Cys wherein X1 represents an Asp residue, a Tyr residue or a Lys residue; X2 represents an amino acid residue other than a Cys residue and a Pro residue, provided that X2 does not represent a Gly residue when X1 represents an Asp residue; wherein functional groups at the N-terminus, C-terminus and side chain are optionally substituted with protecting groups; and wherein each of the amino acid residues are either D-form or L-form.

2. A metal chelate forming peptide according to claim 1, wherein X1 is an amino acid residue having a free amino group at the α-position thereof.

3. A metal chelate forming peptide having an amino acid sequence represented by:

X1-X2-Cys wherein X1 is represents an Asp residue, and X2 is a Tyr residue, wherein functional groups at the N-terminus, C-terminus and side chain are optionally sustituted with protecting groups; and wherein each of the amino acid residues are either D-form or L-form.

4. A metal chelate forming peptide having an amino acid sequence represented by:

X1-X2-Cys wherein X1 is an Asp residue, and X2 is a Lys residue, wherein functional groups at the N-terminus, c-terminus and side chain are opionally substituted with protecting groups; and wherein each of the amino acid residues are either D-form or L-form.

5. A metal chelate forming peptide having an amino acid sequence represented by:

X1-X2-Cys wherein X1 is a Tyr residue, and X2 is a Gly residue, wherein functional groups at the N-terminus, c-terminus and side chain may be optionally substituted with protecting groups; and wherein each of the amino acid residues are either D-form or L-form.

6. A metal chelate forming peptide having an amino acid sequence represented by:

X1-X2-Cys wherein X1 is a Tyr residue, and X2 is a Tyr residue, wherein functional groups at the N-terminus, C-terminus and side chain are optionally substituted with protecting groups; and wherein each of the amino acid residues may be either D-form or L-form.

7. A metal chelate forming peptide having an amino acid sequence represented by:

X1-X2-Cys wherein X1 is a Tyr residue, and X2 is a Lys residue, wherein functional groups at the N-terminus, C-terminus and side chain are optionally substituted with protecting groups; and wherein each of the amino acid residues may be either D-form or L-form.

8. A metal chelate forming peptide according to claim 1, wherein X1 is a Lys residue, and X2 is a Gly residue.

9. A metal chelate forming peptide according to claim 1, wherein X1 is a Lys residue, and X2 is a Tyr residue.

10. A metal chelate forming peptide according to claim 1, wherein X1 is a Lys residue, and X2 is a Lys residue.

11. A complex of a metal chelate forming peptide according to claims 1, 2, 3, 4, 5, 6, 7, 8, 9, or 10, wherein said complex is represented by the following formula:

X1-X2-Cys-X3 wherein X1 and X2 are as defined above, and wherein x3 represents a physiologically active peptide, protein or other substance, wherein X3 is attached to Cys via the C-terminus of Cys.

12. A complex according to claim 11, wherein the metal chelate forming peptide is bound to a peptide having affinity for a focus site in a mammalian body via the N-terminus of said peptide having affinity for a focus site in a mammalian body.

13. A complex according to claim 12, wherein the peptide is selected from a peptide having affinity for a tumor site, a peptide having affinity for an inflammation site, a peptide having an affinity for an infection site, a peptide having an affinity for an infection and an inflammation site, a peptide having affinity for a thrombus site and a peptide having affinity for a brain disorders site.

14. The complex according to claim 11, wherein said other substance is selected from the group consisting of a neurotransmitter, an antibiotic and a prostaglandin.

* * * * *